United States Patent [19]

Liebl et al.

[11] Patent Number: 4,564,382
[45] Date of Patent: Jan. 14, 1986

[54] PHENOXYALKANOYL DERIVATIVES AND THEIR USE IN PLANT PROTECTION

[75] Inventors: Rainer Liebl, Gersthofen; Reinhard Handte, Gablingen; Hilmar Mildenberger, Kelkheim; Klaus Bauer, Rodgau; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 669,762

[22] Filed: Nov. 8, 1984

[30] Foreign Application Priority Data

Nov. 11, 1983 [DE] Fed. Rep. of Germany ....... 3340770

[51] Int. Cl.$^4$ .................... A01N 43/00; A01N 31/00; C07D 265/30; C07D 211/60
[52] U.S. Cl. ..................... 71/88; 260/453.4; 260/453.9; 260/465 D; 544/163; 544/168; 544/400; 546/230; 546/231; 548/568; 564/504; 71/98; 71/121; 71/94; 71/95; 71/92; 71/108; 71/109; 71/110; 71/118; 71/100
[58] Field of Search ............ 260/453.4, 453.9, 465 D; 544/163, 168, 400; 546/230, 231; 548/568; 564/504; 71/98, 121, 94, 95, 88, 92, 108, 109, 110, 118, 100

[56] References Cited

U.S. PATENT DOCUMENTS 4,320,142  3/1982  Black et al. ..................... 260/453.4

OTHER PUBLICATIONS

Noller, Textbook of Organic Chemistry, W. B. Saunders Company, Philadelphia, 1966, pp. 227, 199.

Primary Examiner—Henry R. Jiles
Assistant Examiner—Robert C. Whittenbaugh
Attorney, Agent, or Firm—Curtis, Morris & Safford

[57] ABSTRACT

Compounds of the formula I

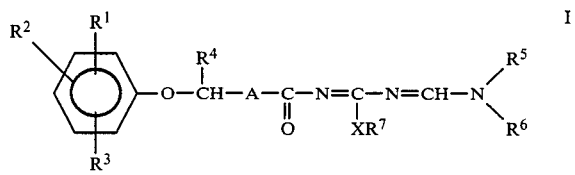

in which $R^1$, $R^2$ and $R^3$ independently of one another denote hydrogen, F, Cl, Br or $(C_1-C_4)$-alkyl, and $R^1$ also denotes $CF_3$, CN, $NO_2$ or alkoxycarbonyl, A denotes a direct bond, $-CH_2-CH_2-$ or $-CH=CH-$, X denotes O, S or $N-R^8$, $R^4$ denotes H or alkyl, $R^5$ and $R^6$ denote alkyl, $R^7$ denotes alkyl, (substituted) benzyl and/or (substituted) phenethyl and $R^8$ denotes H or alkyl or, together with $NR^7$, denotes a heterocyclic ring, are active herbicides and antidotes.

14 Claims, No Drawings

PHENOXYALKANOYL DERIVATIVES AND THEIR USE IN PLANT PROTECTION

The present invention relates to novel compounds of the general formula I

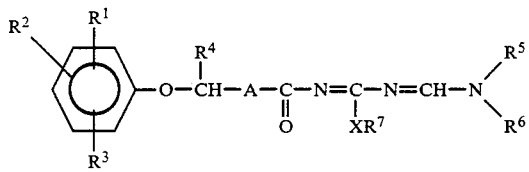

in which

R$^1$, R$^2$ and R$^3$ independently of one another denote hydrogen, F, Cl, Br or (C$_1$-C$_4$)-alkyl; and R$^1$ also denotes CF$_3$, CN, NO$_2$ or COO-(C$_1$-C$_4$)-alkyl;

A denotes a direct bond, —CH$_2$—CH$_2$— or —CH=CH—;

X denotes O, S or NR$^8$;

R$^4$ denotes H or (C$_1$-C$_4$)-alkyl;

R$^5$ and R$^6$ denote identical or different (C$_1$-C$_4$)-alkyl radicals;

R$^7$ denotes (C$_1$-C$_4$)-alkyl, benzyl or phenethyl, it being possible for the phenyl radicals to be mono- or di-substituted by halogen, CF$_3$, NO$_2$ or (C$_1$-C$_4$)-alkyl; and R$^8$ denotes H or (C$_1$-C$_4$)-alkyl; or R$^7$ and R$^8$, together with the nitrogen atom, denote a pyrrolidine, piperidine, morpholine or piperazine ring, which can optionally be further substituted by 1 or 2 CH$_3$ groups.

Preferred compounds of the general formula I are those in which

R$^1$, R$^2$ and R$^3$ independently of one another denote hydrogen, chlorine, bromine and/or methyl, A represents a direct bond, X denotes oxygen, R$^4$ denotes hydrogen or methyl, R$^5$ and R$^6$ each denote methyl and R$^7$ denotes (C$_1$-C$_4$)-alkyl.

The invention furthermore relates to a process for the preparation of the compounds I, which comprises reacting a compound of the general formula II

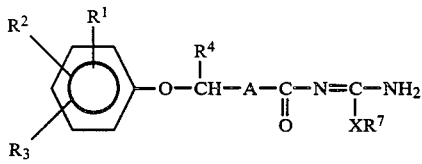

with a dialkylformamide dialkyl acetal of the general formula III

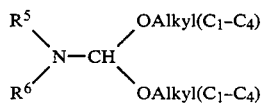

The reaction is carried out in the presence or absence of a diluent, but in the presence of an acid catalyst, it being possible for the temperature to be between 20° C. and 150° C.

The reaction is preferably carried out without a solvent, with concentrated sulfuric acid as the catalyst, at temperatures from 80° to 100° C. Examples of other possible catalysts are glacial acetic acid, acetic anhydride and p-toluenesulfonic acid.

The compounds of the general formula II required for the preparation are prepared by known methods from methylisourea sulfate and the corresponding carboxylic acid chlorides, analogously to U.S. Pat. No. 3,914,224.

Surprisingly, it has been found that compounds of the formula I have the properties on the one hand of having a very good herbicidal action against numerous weeds and on the other hand of reducing and eliminating phytotoxic side effects of plant protection agents, especially of herbicides, when used in crops of useful plants.

Compounds according to the invention thus on the one hand combat weeds in various agricultural crops, that is to say they have very good herbicidal properties and are tolerated, without damage being observed, by crop plants, such as cereals, maize, rice and the like and also broad-leaved crop plants.

On the other hand, they can be applied in low concentrations in combination with other herbicides and are then capable of antagonizing, i.e. completely eliminating, harmful side effects of the latter, without impairing their herbicidal activity.

The field of use of conventional plant protection agents can thereby be quite considerably extended. Those compounds which have the property of protecting crop plants from phytotoxic damage by herbicides, without impairing the actual herbicidal action of these agents, are called "antidotes" or "safeners".

Herbicides of which the phytotoxic side effects can be reduced by means of the compounds of the formula I are, for example, carbamates, thiolcarbamates, halogenoacetanilides, substituted phenoxy- and phenoxyphenoxycarboxylic acid esters and pyridyloxy-, benzoxazolyloxy- and benzothiazolyloxy-phenoxycarboxylic acid esters, dimedone oxime derivatives and furthermore quinolyl-, naphthyl- and quinoxalyl-oxyphenoxycarboxylic acid esters.

Herbicides from the following classes may be mentioned as examples, without imposing a limitation:

(A) Herbicides of phenoxyphenoxycarboxylic acid (C$_1$-C$_4$)-alkyl, (C$_2$-C$_4$)alkenyl and (C$_3$-C$_4$)alkynyl ester type, such as, for example methyl 2-(4-(2,4-dichlorophenoxy)-phenoxy)-propionate, methyl 2-(4-(4-bromo-2-chlorophenoxy)-phenoxy)-propionate, methyl 2-(4-(4-trifluoromethylphenoxy)-phenoxy)-propionate, methyl 2-(4-(2-chloro-4-trifluoromethylphenoxy)-phenoxy)-propionate, methyl 2-(4-(2,4-dichlorobenzyl)-phenoxy)-propionate, ethyl 4-(4-(4-trifluoromethylphenoxy)-phenoxy)-pent-2-enoate, ethyl 2-(4-(3,5-dichloropyridyl-2-oxy)-propionate, propargyl 2-(4-(3,5-dichloropyridyl-2-oxy)-phenoxy)-propionate, ethyl 2-(4-(6-chlorobenzoxazol-2-yloxy)-phenoxy)-propionate, ethyl 2-(4-(6-chlorobenzothiazol-2-yloxy)-phenoxy)-propionate, methyl 2-(4-(3-chloro-5-trifluoromethyl-2-pyridyloxy)-phenoxy)-propionate, butyl 2-(4-(5-trifluoromethyl-2pyridyloxy)-phenoxy)-propionate and ethyl 2-(4-(6-chloro-2-quinoxalinyloxy)-phenoxy)-propionate.

(B) Chloroacetanilide herbicides, such as, for example,
N-methoxymethyl-2,6-diethyl chloroacetanilide,
N-(3'-methoxyprop-2'-yl)-2-methyl-6-ethyl chloroacetanilide and
N-(3-methyl-1,2,4-oxadiazol-5-ylmethyl)-chloroacetic acid 2,6-dimethylanilide.

(C) Thiolcarbamates, such as, for example
S-ethyl N,N-dipropylthiocarbamate or
S-ethyl N,N-diisobutylthiocarbamate.

(D) Dimedone derivatives, such as, for example
2-(N-ethoxybutyrimidoyl)-5-(2-ethylthiopropyl)-3-hydroxy-2-cyclohexen-1-one,
2-(N-ethoxybutyrimidoyl)-5-(2-phenylthiopropyl)-3-hydroxy-2-cyclohexen-1-one or
2-(1-allyloxyiminobutyl)-4-methoxycarbonyl-5,5-dimethyl-3-oxocyclohexenol.

For application, the compounds of the formula I can be formulated, with the customary formulation auxiliaries, as dusting agents, wettable powders, dispersions, emulsion concentrates and the like containing the active substance in concentrations of 2–80%, and can either be used as such (dusting agents or pellets) or be dissolved or dispersed in a solvent (water) before application.

The ratio of antidote:herbicide can vary within wide limits of between 0.01 and 10 parts of antidote per part of herbicide. The particular optimum amounts of herbicide and antidote depend on the type of herbicide or antidote used and on the nature of the plant crop to be treated, and can be determined from case to case by corresponding experiments.

The main fields of use for the agents according to the invention are chiefly crops of cereals (wheat, rye, barley and oats), rice, maize and sorghum, but also cotton, sugar beet, sugar cane, soybean and the like.

Depending on their properties, the agents according to the invention can be used for pretreating the seed of the crop plants (seed dressing) or before sowing in the seed furrows or as a tank mix before or after emergence of the plants. Pre-emergence treatment includes both the treatment of the cultivated area before sowing and the treatment of the sown cultivated areas on which there is not yet growth.

In principle, the antidote can be applied before, after or at the same time as a herbicide, but simultaneous application in the form of tank mixes or, if appropriate, finished formulations is preferred.

The agents according to the invention can be used as wettable powders, emulsifiable concentrates, solutions which can be sprayed, dusting agents, dressing agents, dispersions, granules or microgranules in the usual formulations.

Wettable powders are products which are uniformly dispersible in water and which, in addition to the active substance and apart from a diluent or inert substance, if appropriate, also contain wetting agents, for example polyoxyethylated alkylphenols, polyoxyethylated fatty alcohols, or alkyl- or alkylphenyl-sulfonates, and dispersing agents, for example sodium lignin-sulfonate, sodium 2,2'-dinaphthylmethane-6,6'-disulfonate, sodium dibutylnaphthalenesulfonate or sodium oleyl-methyl-tauride. They are prepared in the customary manner, for example by grinding and mixing the components.

Emulsifiable concentrates can be prepared, for example, by dissolving the active substance in an inert organic solvent, for example butanol, cyclohexanone, dimethylformamide, xylene or higher-boiling aromatics or hydrocarbons, with the addition of one or more emulsifiers. In the case of liquid active substances, all or some of the solvent content can also be dispensed with. Examples of emulsifiers which can be used are: calcium alkyl-arylsulfonates, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxyethylene sorbitan fatty acid esters or polyoxyethylene sorbitol esters.

Dusting agents can be obtained by grinding the active substance with finely divided, solid substances, for example talc or natural clays, such as kaolin, bentonite, pyrophilite or diatomaceous earth.

Granules can be prepared either by spraying the active substance onto adsorbent, granular inert material or by applying active substance concentrates to the surface of carriers, such as sand or kaolinites, or granular inert material by means of binders, for example polyvinyl alcohol, sodium polyacrylate or mineral oils. Suitable active substances can also be granulated in the customary manner for the preparation of fertilizer granules, if desired as a mixture with fertilizers.

The active substance concentration in wettable powders is, for example, about 10 to 90% by weight, the remainder to make up to 100% by weight consisting of the usual formulation constituents. The active substance concentration in emulsifiable concentrates can be about 10 to 80% by weight. Dust-like formulations usually contain 5 to 20% by weight of active substance, and solutions which can be sprayed contain about 2 to 20% by weight. The active substance content in granules depends partly on whether the active compound is present in the liquid or solid form and on which granulation auxiliaries, fillers and the like are used.

The active substance formulations also contain, if appropriate, the particular customary tackifiers, wetting agents, dispersing agents, emulsifying agents, penetration agents, solvents, fillers or carriers.

For application, the concentrates in the commercially available form are diluted, if appropriate, in the customary manner, for example by means of water in the case of wettable powders, emulsifiable concentrates, dispersions and sometimes also microgranules. Dust-like and granular formulations and solutions which can be sprayed are usually not further diluted with additional inert substances before application.

Mixtures or mixed formulations with other active substances, such as, for example, insecticides, acaricides, herbicides, fertilizers, growth regulators or fungicides, are also possible, where relevant.

Some formulation examples are described below:

A dusting agent is obtained by mixing 10 parts by weight of active substance and 90 parts by weight of talc or inert substance, and comminuting the mixture in an impact mill.

A powder which is readily dispersible and wettable in water is obtained by mixing 25 parts by weight of active substance, 64 parts by weight of kaolin-containing quartz, as an inert substance, 10 parts by weight of potassium lignin-sulfonate and 1 part by weight of sodium oleyl-methyl-tauride, as a wetting agent and dispersing agent, and grinding the mixture in a pinned disc mill.

A dispersion concentrate which is readily dispersible in water is obtained by mixing 20 parts by weight of active substance with 6 parts by weight of alkylphenol polyglycol ether (Triton X 207), 3 parts by weight of isotridecanol polyglycol ether (8 moles of ethylene oxide) and 71 parts by weight of paraffinic mineral oil (boiling range, for example about 255° to above 377° C.), and grinding the mixture to a fineness of less than 5 microns in a ball mill.

An emulsifiable concentrate is obtained from 15 parts by weight of active substance, 75 parts by weight of cyclohexanone, as a solvent, and 10 parts by weight of oxyethylated nonylphenol, as an emulsifier.

A. PREPARATION EXAMPLES

EXAMPLE 1

N-(2,4-Dichlorophenoxyacetyl)-N'-dimethylaminomethylene-O-methyl-isourea

½ ml of concentrated sulfuric acid is added to 28 g (0.1 mole) of N-(2,4-dichlorophenoxyacetyl)-O-methyl-isourea (c.f. Example 1A) and 16.2 g (0.11 mole) of dimethylformamide diethyl acetal and the mixture is rapidly heated to 100° C., with stirring. As soon as the solution starts to boil, the heating is removed and the mixture is allowed to cool to room temperature. The crystals precipitated are stirred with 50 ml of ether, filtered off with suction and dried overnight. 24 g (72% of theory) of N-(2,4-dichlorophenoxyacetyl)-N'-dimethylaminomethylene-O-methyl-isourea are obtained in the form of colorless crystals of melting point 105°–106° C.

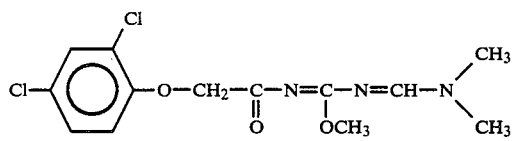

The compounds of Table 1 are prepared in an analogous manner.

TABLE 1

| Example No. | (R)$_n$ | R$^4$ | XR$^7$ | Melting point (°C.) |
|---|---|---|---|---|
| 2 | 3,3-Cl$_2$ | H | OCH$_3$ | 110–112 |
| 3 | H | H | OCH$_3$ | 72–73 |
| 4 | 3,4-Cl$_2$ | CH$_3$ | OCH$_3$ | Oil |
| 5 | 2,5-Cl$_2$ | H | OCH$_3$ | 144–147 |
| 6 | 4-Cl, 3-CH$_3$ | H | OCH$_3$ | 117–119 |
| 7 | 4-Cl, 2-CH$_3$ | H | OCH$_3$ | 89–90 |
| 8 | 2-i-C$_3$H$_7$, 5-CH$_3$ | H | OCH$_3$ | Oil |
| 9 | 2,6-Cl$_2$, 4-CH$_3$ | H | OCH$_3$ | 141–145 |
| 10 | 2,4,6-(CH$_3$)$_3$ | H | OCH$_3$ | 130–131 |
| 11 | 4-Cl | H | OCH$_3$ | 92–94 |
| 12 | 2-CO$_2$Et | H | OCH$_3$ | Oil |
| 13 | 3-CO$_2$Et | H | OCH$_3$ | Oil |
| 14 | 2,3-(CH$_3$)$_2$ | H | OCH$_3$ | 103–105 |
| 15 | 4-Cl, 3,5-(CH$_3$)$_2$ | H | OCH$_3$ | 94–95 |
| 16 | 2-CH$_3$ | H | OCH$_3$ | Oil |
| 17 | 3,5-Cl$_2$ | H | OCH$_3$ | 142–144 |
| 18 | 2,4-Cl$_2$ | H | OC$_2$H$_5$ | 106–107 |
| 19 | 4-Cl, 2-CH$_3$ | H | OC$_2$H$_5$ | 72–73 |
| 20 | 2,3-(CH$_3$)$_2$ | H | OC$_2$H$_5$ | 58–60 |
| 21 | 4-Cl, 3,5(CH$_3$)$_2$ | H | OC$_2$H$_5$ | 82–84 |
| 22 | 3,4-Cl$_2$ | H | OC$_2$H$_5$ | 104–106 |
| 23 | 2,4-Cl$_2$ | H | SCH$_3$ | 104–105 |
| 24 | 4-Cl | H | SCH$_3$ | 98–100 |
| 25 | 4-Cl, 3,5-(CH$_3$)$_2$ | H | OCH$_3$ | 88–92 |
| 26 | 4-CF$_3$ | H | OCH$_3$ | |
| 27 | 4-CN | H | OCH$_3$ | |
| 28 | 3-NO$_2$ | H | OCH$_3$ | |
| 29 | 4-COOC$_2$H$_5$ | H | OC$_2$H$_5$ | |

EXAMPLE 30

1-(2,4-Dichlorophenoxyacetyl)-3-dimethylaminomethylene-4-tetramethylene-guanidine 8.1 g (0.055 mole) of dimethylformamide diethyl acetal and 15.8 g (0.5 mole) of 1-(2,4-dichlorophenoxyacetyl)-3-tetramethylene-guanidine are warmed to 100° C. with 0.3 ml of concentrated sulfuric acid for 5 minutes. The volatile constituents are distilled off at 60° C./0.01 bar. 16 g (86% of theory) of 1-(2,4-dichlorophenoxyacetyl)-3-dimethylaminomethylene-4-tetramethylene-guanidine remain in the form of a viscous, yellow oil.

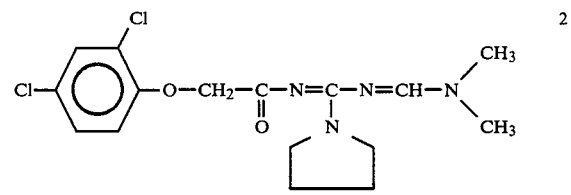

The following compounds are obtained analogously:

TABLE 2

| Example No. | (R)$_n$ | R$^1$ | R$^7$ | R$^8$ | Melting point (°C.) |
|---|---|---|---|---|---|
| 31 | 2,4-Cl$_2$ | H | \multicolumn{2}{l}{tetrahydropyran-2,6-diyl-dimethyl} | Oil |
| 32 | 2,4-Cl$_2$ | H | H | —CH$_2$CH$_2$—OCH$_3$ | Oil |

EXAMPLE 1A (Preparation of the starting substances II)

N-(2,4-Dichlorophenoxyacetyl)-O-methyl-isourea 13.5 g (0.11 mole) of O-methyl-isourea sulfate are dissolved in 50 ml of water and 100 ml of methylene chloride. 16 g of 50% strength aqueous sodium hydroxide solution (0.2 mole) and 24 g (0.1 mole) of 2,4-dichlorophenoxyacetyl chloride are simultaneously added dropwise from two separate vessels at 0° C., with vigorous stirring. The mixture is stirred at 0° C. for 1 hour and at 40° C. for 3 hours and the organic phase is separated off, washed twice with 100 ml of water and dried over sodium sulfate.

After the solvent has been distilled off, 22 g (79% of theory) of N-(2,4-dichlorophenoxyacetyl)-O-methylisourea remain in the form of colorless crystals of melting point 104° C.

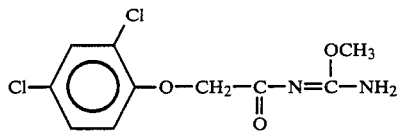

The other compounds of the formula II were obtained in an analogous manner.

C. BIOLOGICAL EXAMPLES

I. Safener action

Wheat was grown to the 5-leaf stage in a greenhouse in pots of 9 cm φ and was then sprayed with a herbicide and a compound according to the invention until dripping wet. 3 weeks after the treatment, the plants were evaluated for any type of damage by the products, the extent of the sustained inhibition of growth being particularly taken into consideration.

The results from Table 3 illustrate that the compounds according to the invention can very effectively reduce severe herbicidal damage.

Mixtures of herbicides and compounds according to the invention are thus suitable for selectively combating weeds in cereals.

| Compound | Dose in kg of active substance/ha | % damage to wheat |
|---|---|---|
| Herbicide F* | 2.0 | 70 |
| F + Example 1 | 2.0 + 2.5 | 30 |
| F + Example 2 | 2.0 + 2.5 | 20 |
| F + Example 6 | 2.0 + 2.5 | 30 |
| F + Example 18 | 2.0 + 2.5 | 30 |

*(F = fenoxaprop-ethyl = ethyl 2-[4-(6-chloro-2-benzoxazolyloxy)-phenoxy]-propionate)

The degree of safener action of other compounds was found to be quite similar when amounts of 2.5 kg of active substance/ha were applied.

The herbicidal activity of fenoxaprop-ethyl was not impaired by the addition of the safeners according to the invention; in the stated application amounts of, for example, 2.0 kg of active substance/ha, it was always 100%, for example on *Alopecurus myosuroides*, on *Avena fatua* and on sorghum, such as Echinochloa and Setaria species.

BIOLOGICAL EXAMPLE 2

Wheat, barley and the two important harmful grasses *Avena fatua* and *Alopecurus myosuroides* were sown and were grown to the 4-leaf stage under greenhouse conditions. The compounds according to the invention and a herbicide were then sprayed onto the test plants in various dosages. After standing for a further 4 weeks in the greenhouse, the plants were evaluated for any type of inhibition or damage in comparison with untreated control plants. The results (Table 4) illustrate that the compound according to the invention very greatly reduces or completely eliminates harmful herbicidal effects to wheat and barley, without impairing the herbicidal activity against the harmful grasses Avena and Alopecurus.

TABLE 4

Safener action in the post-emergence method on barley and wheat. Damage in %, in corparison with untreated control plants.

| Compound | Dose (kg of active substance/ha) | HV | TA | AVF | ALM |
|---|---|---|---|---|---|
| F + Example 1 | 1.6 + 0.125 | — | 23 | | |
| | 0.8 + 0.125 | — | 10 | | |
| | 0.4 + 0.125 | 60 | 0 | — | 100 |
| | 0.2 + 0.125 | 23 | 0 | 99 | 97 |
| | 0.1 + 0.125 | 3 | | 99 | 97 |
| | 0.05 + 0.125 | 0 | | 97 | 95 |
| F + Example 1 | 1.6 + 0.5 | | 0 | | |
| | 0.8 + 0.5 | | 0 | | |
| | 0.4 + 0.5 | 15 | 0 | | 100 |
| | 0.2 + 0.5 | 0 | 0 | 99 | 99 |
| | 0.1 + 0.5 | 0 | | 99 | 99 |
| | 0.05 + 0.5 | 0 | | 96 | 97 |
| F | 1.6 | — | 70 | | |
| | 0.8 | — | 55 | | |
| | 0.4 | 85 | 45 | | 99 |
| | 0.2 | 75 | 20 | 99 | 97 |
| | 0.1 | 65 | — | 99 | 95 |
| | 0.05 | 50 | — | 93 | 88 |
| Example 1 | 0.5 | 0 | 0 | 0 | 0 |

HV = barley
TA = wheat
AVF = *Avena fatua*
ALM = *Alopecurus myosuroides*

II. Herbicidal action

When applied in higher amounts, the compounds according to the invention exhibit good herbicidal properties against dicotyledonous and, in some cases, especially in the pre-emergence method, against monocotyledonous weeds. They are therefore suitable for selectively combating weeds in agricultural crops where use by both the pre-emergence method and the post-emergence method is possible, and in particular in cereal crops and in broad-leaved crops, such as soybean, cotton or sugar beet.

BIOLOGICAL EXAMPLE 3

Broad-leaved and graminaceous weeds were sown on loam soil in plastic pots of 9 cm φ and were treated with the compounds according to the invention both by the pre-emergence method and by the post-emergence method (amount applied in each case 2.4 kg of active substance/ha). 4 weeks later, the herbicidal activity was estimated by visual rating.

The results (Table 5) show that the compounds according to the invention combat a broad spectrum of weeds by the pre-emergence and post-emergence method.

TABLE 5

| Example No. | Herbicidal activity (damage in %) | | | | | | |
|---|---|---|---|---|---|---|---|
| | Pre-emergence | | | | Post-emergence | | |
| | SIA | STM | CRS | LOM | SIA | AMR | STM |
| 1 | 5 | 5 | 5 | 5 | 5 | 5 | 15 |
| 3 | 5 | 5 | 3 | 4 | 5 | 5 | 5 |
| 2 | 5 | 5 | 5 | 5 | 5 | 5 | 5 |
| 5 | 5 | 5 | 5 | 5 | 5 | 5 | 5 |
| 6 | 5 | 5 | 5 | 5 | 5 | 5 | 4 |
| 7 | 5 | 5 | 5 | 5 | 5 | 5 | 5 |
| 8 | — | 3 | — | 3 | 3 | — | 4 |
| 23 | 5 | 5 | 5 | 5 | 5 | 5 | 5 |
| 18 | 5 | 3 | 5 | 5 | 3 | 5 | 5 |
| 19 | 5 | 5 | 5 | 5 | 5 | 5 | 5 |
| 20 | 5 | 5 | 5 | 4 | 3 | — | 4 |

TABLE 5-continued

| | Herbicidal activity (damage in %) | | | | | | |
|---|---|---|---|---|---|---|---|
| Example | Pre-emergence | | | | Post-emergence | | |
| No. | SIA | STM | CRS | LOM | SIA | AMR | STM |
| 10 | 3 | 3 | 3 | 2 | 3 | 4 | 3 |

SIA = *Sinapis arvensis*
STM = *Stellaria media*
CRS = *Chrysanthemum segetum*
LOM = *Lolium multiflorum*
AMR = *Amaranthus retroflexus*
Rating key:
1 = 0–20% action
2 = 20–40% action
3 = 40–60% action
4 = 60–80% action
5 = 80–100% action

We claim:

1. A compound of the formula I

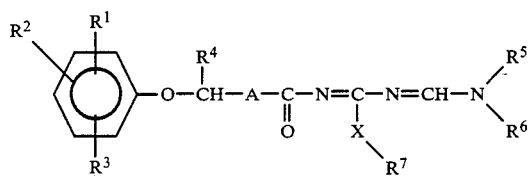

in which

R$^1$, R$^2$ and R$^3$ independently of one another are hydrogen, F, Cl, Br or (C$_1$–C$_4$)-alkyl; and R$^1$ also is CF$_3$, CN, NO$_2$ or COO-(C$_1$–C$_4$)-alkyl;

A is a direct bond, —CH$_2$—CH$_2$— or —CH=CH—;

X is O, S or NR$^8$;

R$^4$ is H or (C$_1$–C$_4$)-alkyl;

R$^5$ and R$^6$ are identical or different (C$_1$–C$_4$)-alkyl radicals;

R$^7$ is (C$_1$–C$_4$)-alkyl, benzyl or phenethyl, the phenyl radicals being unsubstituted or mono- or di-substituted by halogen, CF$_3$, NO$_2$ or (C$_1$–C$_4$)-alkyl; and R$^8$ is H or (C$_1$–C$_4$)-alkyl; or R$^7$ and R$^8$, together with the nitrogen atom, denote a pyrrolidine, piperidine, morpholine or piperazine ring, each ring being unsubstituted or substituted by 1 or 2 CH$_3$ groups.

2. A herbicidal composition comprising an amount of the compound claimed in claim 1 sufficient to exert herbicidal activity and a carrier therefor.

3. An antidotally active composition comprising an amount of the compound claimed in claim 1 sufficient to exert antidotal action and a carrier therefor.

4. A method of protecting crop plants from phytotoxic side effects of herbicides, which comprises treating the plants, parts of plants or soil with an active amount of a compound as claimed in claim 1 before, after or at the same time as the treatment with a herbicide.

5. The method as claimed in claim 4, wherein the herbicide is an active substance from the group of phenoxycarboxylic acid esters, chloroacetanilides, thiolcarbamates or dimedone derivatives.

6. The method as claimed in claim 4, wherein the herbicide originates from the group of phenoxycarboxylic acid esters which are active against grasses.

7. The method as claimed in claim 4, wherein the ratio of herbicide:antidote is in the range from 1:0.01 to 1:10.

8. A method of combating harmful plants, which comprises applying a herbicidally active amount of a compound as claimed in claim 1 to the cultivated areas to be treated.

9. A compound as claimed in claim 1 which is

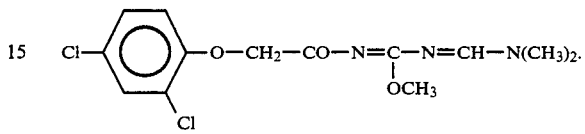

10. A compound as claimed in claim 1 which is

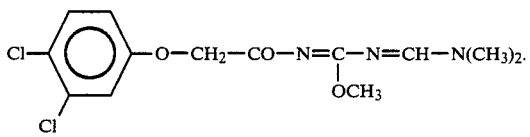

11. A compound as claimed in claim 1 which is

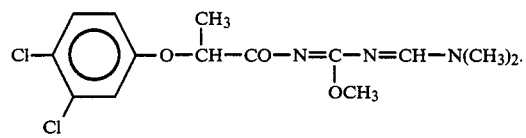

12. A compound as claimed in claim 1 which is

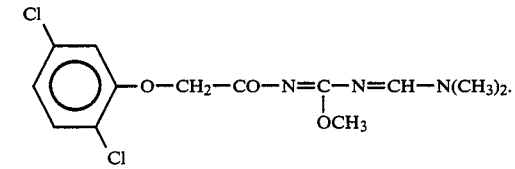

13. A compound as claimed in claim 1 which is

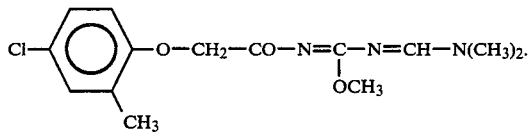

14. A compound as claimed in claim 1 which is

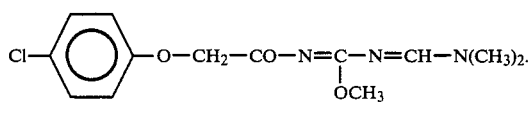

* * * * *